(12) United States Patent
Weiβ et al.

(10) Patent No.: US 9,173,573 B2
(45) Date of Patent: Nov. 3, 2015

(54) IMAGING AN OBJECT OF INTEREST (75) Inventors: Steffen Weiβ, Hamburg (DE); Tobias Schaffter, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1323 days.

(21) Appl. No.: 11/816,639

(22) PCT Filed: Feb. 13, 2006

(86) PCT No.: PCT/IB2006/050454
§ 371 (c)(1),
(2), (4) Date: Aug. 20, 2007

(87) PCT Pub. No.: WO2006/090298
PCT Pub. Date: Aug. 31, 2006

(65) Prior Publication Data
US 2008/0154130 A1    Jun. 26, 2008

(30) Foreign Application Priority Data
Feb. 23, 2005  (EP) .................................... 05101348

(51) Int. Cl.
*A61B 8/14*    (2006.01)
*A61B 5/00*    (2006.01)
*A61B 8/00*    (2006.01)
(52) U.S. Cl.
CPC .............. *A61B 5/0097* (2013.01); *A61B 5/0048* (2013.01); *A61B 5/0073* (2013.01); *A61B 8/4416* (2013.01); *A61B 5/6848* (2013.01); *A61B 8/14* (2013.01)

(58) Field of Classification Search
CPC .. A61B 5/0073; A61B 5/0048; A61B 5/0097; A61B 8/4416; A61B 8/14
USPC .................................................. 600/437, 476
See application file for complete search history.

(56) References Cited

U.S. PATENT DOCUMENTS

| 5,086,620 A | 2/1992 | Spears |
| 5,941,825 A * | 8/1999 | Lang et al. .................... 600/449 |
| 6,033,645 A | 3/2000 | Unger et al. |
| 6,106,474 A | 8/2000 | Koger et al. |
| 6,123,923 A | 9/2000 | Unger et al. |
| 6,716,412 B2 | 4/2004 | Unger |

(Continued)

FOREIGN PATENT DOCUMENTS

| DE | 19654053 A1 | 6/1998 |
| EP | 1602381 A1 | 12/2005 |
| WO | 9857666 A1 | 12/1998 |
| WO | 2006027738 A1 | 3/2006 |

OTHER PUBLICATIONS

C.J.Harvey et al; "Advances in Ultrasound", Clinical Radiology, 57, pp. 157-177, 2002.

(Continued)

*Primary Examiner* — Long V Le
*Assistant Examiner* — Angela M Hoffa (57) ABSTRACT

An apparatus for imaging an object of interest includes an ultrasound device configured to emit ultrasonic waves of at least two different frequencies onto the object of interest, and an electromagnetic radiation detector configured to detect electromagnetic fluorescence radiation emitted by the object of interest in response to an absorption of primary electromagnetic radiation and in response to the ultrasonic waves.

28 Claims, 4 Drawing Sheets

(56) References Cited

U.S. PATENT DOCUMENTS

| | | | |
|---|---|---|---|
| 6,748,259 B1 | 6/2004 | Benaron et al. | |
| 7,098,039 B1* | 8/2006 | Lloyd et al. | 436/172 |
| 2005/0131289 A1* | 6/2005 | Aharoni et al. | 600/407 |
| 2005/0169348 A1* | 8/2005 | Chen et al. | 374/161 |
| 2005/0169843 A1* | 8/2005 | Weissleder et al. | 424/9.6 |
| 2005/0255044 A1* | 11/2005 | Lomnes et al. | 424/9.6 |
| 2007/0092447 A1* | 4/2007 | Padilla De Jesus et al. | 424/9.1 |
| 2008/0077002 A1* | 3/2008 | Nielsen et al. | 600/407 |

OTHER PUBLICATIONS

Nico De Jong et al; "Ultrasoncs" 34, pp. 587-590, 1996.

Fabrizio Calliada et al; "Ultrasound Contrast Agents", European Journal of Radiology 27, pp. S157-S160, 1998.

C. M. Moran; et al; Ultrasound in Medicine and Biology, vol. 28, No. 6, pp. 785-791, 2002.

Demos S et al: "In Vivo Targeting of Acoustically Reflective Liposomes", Journal of the American College of Cardiology, vol. 33, No. 3, pp. 867-875, 1999.

Leidy et al: "Lateral Organization and Domain Formation", Biophysical Journal, vol. 80, pp. 1819-1828, 2001.

Wong and Groves: "Molecular Topography Imaging", Proc. Natl. Acad., PNAS, vol. 99, No. 22, pp. 14147-14152, 2002.

John et al: "Rapid Transbilayer Movement", Biophysical Journal, vol. 83, pp. 1525-1534, 2002.

A. Korpel: "Acousto-Optics", Marcel Dekker Inc., 1997.

* cited by examiner

IMAGING AN OBJECT OF INTEREST

The invention relates to the field of imaging. In particular, the invention relates to an apparatus, to an array and to a method for imaging an object of interest, to a use of a particle comprising an acceptor and/or a donor for an apparatus, an array or a method for imaging an object of interest, to a computer-readable medium, and to a program element.

Several techniques exist for diagnostic imaging of a body part, including ultrasound imaging and fluorescence imaging. A major problem in fluorescence imaging in turbid media (e.g. tissue) is that spatial resolution is very poor due to strong scattering of both the excitation light and the emitted fluorescence light. Consequently, the resolution of conventional optical fluorescence tomography is limited.

Lack of modulation is another problem that is encountered when using light (e.g. fluorescence light) as an imaging tool. It is known to reproduce images by reconstruction images created by a combination of acoustic waves and illumination, see the book "Acousto-optics" by A. Korpel, Marcel Dekker Inc. 1997. In such methods, the change of refractive index caused by acoustic waves is visualized by the effect of the change on refractive index on incident light. However, the change in index caused by acoustic waves is small and the image is of poor quality.

Another method which allows changes in light intensity involves modifying the distance between partners of a fluorescence donor/acceptor pair. The donor molecules absorb excitation light but do not emit fluorescence. If a donor is sufficiently close to an acceptor, the energy is transferred to the acceptor by so-called fluorescence resonance energy transfer (FRET), or more generally due to direct dipole-dipole interaction, and the acceptor emits fluorescence. The fluorescence intensity depends thus on the distance between donor and acceptor. Fluorescence resonance energy transfer (FRET) is a phenomenon which is strongly dependent on the distance (proportional $r^{-6}$) between donor and acceptor. The transition from no to very effective energy transfer is very sharp, i.e. a high-fluorescence modulation can be achieved. FRET has been used in biological applications for determining the binding between proteins or to study membrane structures or to study interactions between membranes. For those purposes, vesicles were developed which contain a fluorescence donor and/or acceptor for FRET (Wong and Groves 2002 Proc. Natl. Acad. USA 99, 14147-14152; John et al. 2002 Biophys. J. 83, 1525-1534; Leidy et al 2001 Biophys. J. 80, 1819-1828).

Ultrasound micro bubble vesicles comprising fluorescence groups are known, for instance, from U.S. Pat. No. 6,123,923.

It is an object of the invention to enable imaging of an object of interest with sufficient accuracy.

In order to achieve the object defined above, an apparatus, an array and a method for imaging an object of interest, a use of a particle comprising an acceptor and/or a donor, a computer-readable medium and a program element with the features according to the independent claims are provided.

According to an exemplary embodiment of the invention, an apparatus for imaging an object of interest is provided which comprises an ultrasound device adapted to emit ultrasonic waves of at least two different frequencies onto the object of interest, and an electromagnetic radiation detector adapted to detect electromagnetic fluorescence radiation emitted by the object of interest in response to an absorption of primary electromagnetic radiation and in response to the ultrasonic waves.

According to another exemplary embodiment of the invention, an array for imaging an object of interest is provided comprising the object of interest and comprising an apparatus having the above-mentioned features for imaging the object of interest.

Moreover, according to another exemplary embodiment of the invention, a method for imaging an object of interest is provided comprising the steps of emitting ultrasonic waves of at least two different frequencies onto the object of interest, and detecting electromagnetic fluorescence radiation emitted by the object of interest in response to an absorption of primary electromagnetic radiation and in response to the ultrasonic waves.

Beyond this, according to another exemplary embodiment of the invention, the use of a particle is taught, the particle being attachable to an object of interest and comprising a donor adapted to absorb electromagnetic radiation and/or an acceptor for emitting electromagnetic fluorescence radiation for an apparatus, for an array or for a method having the above-mentioned features for imaging the object of interest.

Moreover, a computer-readable medium is provided, in which a computer program for imaging an object of interest is stored which, when being executed by a processor, is adapted to carry out the above-mentioned method steps.

Further, according to another exemplary embodiment of the invention, a program element for imaging an object of interest is provided, which, when being executed by a processor, is adapted to carry out the above-mentioned method steps.

The imaging of an object of interest according to the invention can be realized by a computer program, i.e. by software, by using one or more special electronic optimization circuits, i.e. in hardware, or in hybrid form, i.e. by means of software components and hardware components.

The characterizing features according to the invention particularly have the advantage that an imaging system is provided which is based on the emission of multi-frequency ultrasonic waves towards an object of interest, in combination with the absorption and fluorescence of electromagnetic radiation by the object of interest. An emission of ultrasonic waves of different frequencies to different portions of the object has the effect that a mechanical vibration of the portions of the object of interest is induced with a characteristic frequency, wherein this mechanical oscillation frequency modulates the emission characteristics of the electromagnetic fluorescence radiation of the respective portion. Consequently, the mechanical vibration state of the different portions of the object of interest is different which yields different characteristics of fluorescence radiation of the different portions. Since different portions of the object of interest are influenced by ultrasonic waves having different frequencies, the fluorescence signal of the different portions is modulated accordingly. As a result, a frequency analysis of the re-emitted electromagnetic fluorescence radiation spectrum allows to distinguish between fluorescence contributions originating from the different portions of the object. Thus, a spatially resolved reproduction of the physical structure of the object of interest is enabled.

When material of the object of interest is excited by primary electromagnetic radiation (e.g. light from the environment or from a light source), and when portions of the object of interest are brought into mechanical vibration by ultrasonic waves of different frequencies, then an electromagnetic fluorescence detection signal is detectable which has encoded an information concerning the structure of the object of interest. Such information is included in the ultrasonic modulation frequency and in the intensity of different contributions of the measured signal.

In particular, when ultrasonic waves having different frequencies impinge on different positions of a sample, then the optical signal re-emitted in response to previously absorbed excitation radiation, which optical signal may be detected by an optical detector, has overlaid frequency components which can be assigned to different positions of the object of interest, thus allowing to re-calculate unambiguously the structure of the object of interest.

One or more donor/acceptor pairs may be provided on the object of interest, wherein the donor may be adapted to absorb excitation light, and the acceptor may be provided to interact with the donor in such a manner that the donor transfers energy to the acceptor so that the acceptor may emit fluorescence light. This transfer may depend on the current distance between donor and acceptor. An energy transfer may be switched on when the distance is sufficiently small, an energy transfer may be switched off when the distance is sufficiently large. When the distance between donor and acceptor is modulated by the vibration induced by the ultrasonic sound, then the re-emitted fluorescence signal is modulated accordingly. Thus, the detection signal pattern is characteristically modified in accordance with the frequency of the ultrasonic waves impinging on a corresponding portion of the object, so that the frequency pattern detected by the detector allows to reconstruct the (three-dimensional) structure of the object under investigation.

The imaging system according to the invention allows fast parallel imaging with ultrasonic activatable (e.g. optical) probes. Thus, high resolution (optical) fluorescence imaging is enabled. According to an exemplary embodiment of the invention, micro-bubbles are attached to the object of interest, which micro-bubbles are fluorescent only during exposure to an ultrasonic focus, so that effectively the size of the ultrasonic focus defines the resolution of imaging. Since the multi-frequency transducer according to the invention is capable of emitting ultrasonic waves having different frequencies, it is dispensable according to the invention that a given field of view must be scanned point by point. Consequently, the time needed for the measurement procedure is significantly reduced. According to the invention, an imaging method is disclosed which allows to parallelize the imaging process resulting in a huge reduction of acquisition times.

One aspect according to the invention is to apply an arrangement of ultrasonic foci to a field of view (FOV) simultaneously and to use frequency encoding in order to attribute optical signals originating from the field of view to the foci themselves. This is possible, since the optical fluorescence signal from a specific ultrasonic focus is modulated with the frequency of the ultrasonic field at the position at this particular ultrasonic focus.

Thus, one or more ultrasonic transducers simultaneously emit or emits two or more ultrasonic fields of distinct frequencies $f1, f2, \ldots$, which are designed to form two or more foci adjacent along an extension direction of the object under consideration. Each of these foci then emits an optical fluorescence signal, which is modulated by the respective ultrasonic frequency. After a detection, an analysis of the frequency structure of the detection signals (which analysis can be carried out using a Fourier transformation) may be performed, allowing to separate each of these frequency components individually. Due to a known or easily derivable relation between focus location and focus frequency (which is controllable by selecting the ultrasonic transducer geometry and operation mode), the optical signal components at frequencies $f1, f2, \ldots$ can be attributed to their source locations.

According to an exemplary embodiment, a large number of foci may be applied acquiring a large portion of the field of use simultaneously. These foci may be arranged in any geometrical pattern, e.g. adjacent along a line, within a cube or a square, or spatially separated in a lattice. Generally, the optical detector does not necessarily need to be spatially resolving, because the ultrasonic field performs spatial resolution via the frequency distribution of the emitted ultrasonic waves. However, using an optical detector having a spatial resolution, any ultrasonic frequency can be used simultaneously for several foci which are further than the distance of the spatial resolution of the optical detector apart.

A measurement time speed-up factor achievable according to the invention depends on the number of simultaneous ultrasonic foci.

The invention allows to use frequency encoding to parallelize optical imaging rather than imaging point by point. An ultrasonic transducer may simultaneously emit two (or more) ultrasonic fields at distant ultrasonic frequencies $f1$ and $f2$, which may be designed to form two foci along an axis along which an object of interest is located. Each of these foci then emits, after having absorbed primary electromagnetic energy, an electromagnetic fluorescence signal, which is modulated by the respective ultrasonic frequency. After a detection, a Fourier transformation resolves these frequency components, which can be attributed to the source locations.

It is an advantage of the system according to the invention that a huge speed up of a high resolution optical fluorescence imaging is achieved. Due to the frequency-resolving parallelization of the imaging process/scanning of different portions of the object under examination, no loss of the signal-to-noise ratio results. The invention has, among others, applications in the field of molecular imaging, optical imaging of tissue, optical tracking in turbid media, etc.

According to an exemplary embodiment, the invention teaches compositions and methods for fluorescence imaging, such as fluorescence tomography. In this context, the invention provides a highly parallelized measurement system which allows, via the use of two, three or more different frequency values of activating ultrasonic waves, to distinguish in the optical measurement spectrum between different parts or portions of the particle to be measured.

According to an aspect of the invention, used particles may show a modulation of emitted fluorescence by a contrast medium by means of changing the distance between fluorescence donor and fluorescence acceptor. By changing the distance, the fluorescence can be turned on, modulated, or turned off. For each frequency of exciting ultrasonic waves, the change of the distance can be controlled individually for each part of the object of interest.

The invention describes a system for combined optical ultrasound imaging in the multi-frequency domain, wherein ultrasound is used for high spatial resolution and the fluorescence detection leads to a high sensitivity. The implementation of different ultrasonic wave frequencies realizes a short measurement time, so that even a measurement on moving objects can be carried out without the danger of motion artifacts.

The object of interest may be provided with donors and/or acceptors or donor and/or acceptor groups for energy exchange via FRET.

An ultrasound field with a plurality of predetermined frequencies can be used to switch the compound or composition of a particular part of the object of interest from a non-fluorescence to a fluorescence state, or vice versa, using for example flexible particles such as vascular flexible particles, for instance micro-bubbles with fluorescence donors and/or fluorescence acceptors.

Thus, a particle can be forced to deform or oscillate by an ultrasound field of a particular frequency, which may be focused. This may result in a characteristic time-dependent change of the distance between a fluorescence donor and a fluorescence acceptor on or in the particle or object of interest. According to an exemplary embodiment, related to FRET, the transition from no (essentially 0%) to very effective (essentially 100%) energy transfer is very sharp, due to the strong dependence of the FRET effect on the distance r (proportional to $r^{-6}$). Thus, a high fluorescence modulation and consequently a high signal-to-noise ratio can be achieved. Using the system according to the invention, the spatial resolution can be limited by the ultrasound focus size which may be in the order of 1 $mm^3$ or less. This may be three orders of magnitude or more better than the resolution of conventional optical fluorescence tomography. According to the invention, this high spatial resolution is combined with a high time resolution. According to the invention, the fluorescence can be generated by FRET, but also by other mechanisms of energy transfer such as excited state reactions.

One exemplary application of the invention relates to the provision of an image of a body part or tissue of an individual having a contrast medium which comprises particles comprising a fluorescence donor and/or a fluorescence acceptor. This may be performed by subjecting the body part or tissue to ultrasound and recording the modulation in fluorescence light emitted by the contrast medium.

According to the apparatus of the invention adapted for ultrasound imaging, an ultrasound multi-frequency source and an apparatus for the detection of emitted fluorescence light is provided. The light emission can be locally modulated by focussing an ultrasound beam, correlated with a particular frequency. A reconstruction unit can be provided for the generation of an image from detected fluorescence light, implementing a frequency analysis to separate individual contributions from different portions of the object investigated. A control unit may control the generation of ultrasound and/or recording of ultrasound with the emission of light by a light source and/or a detection of light recorded. That control unit may also control the emission of ultrasonic waves of different frequencies which are emitted in a manner as to impinge on different parts of an object of interest.

In the following, exemplary embodiments according to the invention will be described.

Next, exemplary embodiments of the apparatus for imaging an object of interest will be described. However, these embodiments apply also for the array and the method for imaging an object of interest, for the use according to the invention, for the program element and for the computer-readable medium.

The ultrasound device of the apparatus may be adapted to emit ultrasonic waves of at least two different frequencies on at least two different portions of the object of interest. In other words, the ultrasonic transducer may be adapted such that both, direction and frequency of particular mechanical wave packets can be adjusted individually, so that it is possible to impinge mechanical waves of different frequency on different foci or portions of the object of interest.

Particularly, the ultrasound device may be adapted to emit ultrasonic waves of at least two different frequencies on at least two different portions of the object of interest concurrently, that is to say in a timely parallel manner. According to this embodiment, the different foci of the object of interest which are to be irradiated with ultrasonic waves of different frequencies, are irradiated simultaneously, so that fluorescence radiation is also emitted essentially simultaneously. However, since the frequency information of the ultrasonic wave is still included in the fluorescence radiation, it is possible, by an appropriate frequency analysis of the detected signals, to distinguish between signals originating from different portions of the object of interest.

The ultrasound device may be adapted to emit ultrasonic waves of at least two different frequencies on at least two different portions of an object of interest in such a manner that electromagnetic fluorescence radiation emitted by the at least two different portions of the object of interest is modulated in accordance with the at least two different frequencies. In other words, by defining a spatial dependence of the frequency of the ultrasonic wave field, a spatial dependence of the frequency of the re-emitted electromagnetic radiation can be adjusted, so that the modulation frequencies of the detection signal contributions allow to re-trace from which part of the investigated volume, that is from which voxel of the object of interest, the detection signal stems.

The ultrasound device may be divided into at least two separate ultrasound sources, wherein each of the at least two separate ultrasound sources may be adapted to emit ultrasonic waves of a particular frequency onto an object of interest. Thus, an array of a plurality of ultrasound devices may be provided, wherein the different ultrasound sources are capable of emitting different ultrasound frequencies and are arranged at a distance from one another. By the geometry of this arrangement, the foci are defined which are irradiated by the ultrasonic radiation.

Still referring to the described embodiment, the at least two separate ultrasound sources may be arranged linearly and spaced from one another. By spacing the at least two separate ultrasound sources and arranging them in a linear order, a one-dimensional spectrum can be taken from the object under consideration. By moving the linear arrangement of ultrasonic sources along a direction essentially perpendicular to the arrangement direction of the different ultrasound sources, a two-dimensional scan of the object of interest can be performed with a one-dimensional mechanical motion.

Alternatively, the at least two separate ultrasound sources may be arranged in a matrix-like manner and spaced from one another. By providing a two-dimensional array of the ultrasound sources, moving parts are completely dispensable for a scan, and a two-dimensional measurement can be carried out with a very short measurement time. For instance, the different ultrasound sources may be arranged on nodes of a two-dimensional lattice, thus properly defining the foci of the different ultrasound sources.

The at least two separate ultrasound devices may be adapted to emit ultrasonic waves of a particular frequency onto an object of interest in such a manner that an amplitude and a phase of the emission of ultrasonic waves is controllable or adjustable separately for each of the at least two separate ultrasound sources. The phase, that is the vibration state, and the amplitude, that is the strength or intensity, of the ultrasound can thus be adjusted individually for each of the ultrasound sources.

The ultrasound device may be realized as a single ultrasound source adapted to emit ultrasonic waves of at least two different frequencies in different spatial directions. According to this embodiment, a single multi-frequency ultrasound source or transducer is provided which emits ultrasound waves into different directions such as to define the different foci of ultrasound waves impinging on the object of interest. This emission of ultrasonic sound to different portions of an object of interest can be performed simultaneously or sequentially.

The ultrasound device may be adapted to emit ultrasonic waves on the object of interest in a manner of one of the group consisting of a continuous manner, a modulated manner and a pulsed manner. By emitting ultrasonic waves in a continuous manner, an intense detection signal is achievable yielding a short measurement time and a proper statistics. By pulsing the emitted ultrasonic waves, the modulation of the emitted fluorescence radiation is pulsed as well, so that an unambiguous assignment of exciting ultrasound and emitted detection signals is achieved.

The electromagnetic radiation detector may be a non-spatially resolving detector. Since it is possible to distinguish, via the modulation frequencies of the detection signals, between the spatial origin of the signals, that is from which portion of an object of interest the detection signals stem, it is not necessary to have an electromagnetic radiation detector which is sensitive to spatial information. Thus, it is sufficient that the detector resolves frequency and/or intensity information.

Alternatively to the described embodiment, the electromagnetic radiation detector may be a spatially resolving detector, wherein at least two of the separate ultrasound sources may be adapted to emit ultrasonic waves of the same frequency onto portions of the object of interest which are separated from one another by such a distance that electromagnetic fluorescence radiation originating from different portions on which ultrasonic waves of the same frequency impinges is spatially distinguished by the electromagnetic radiation detector. According to this embodiment, it is possible to hit different portions of the object of interest at the same time with ultrasonic waves of the same frequency, since the electromagnetic radiation detector has, according to this embodiment, also a spatial resolution. Thus, the object of interest may be divided into segments each having a plurality of the portions, wherein the different portions of a segment are emitted by ultrasonic waves of different frequencies. The spatial resolution of the detector may then equal approximately the dimension of a segment, so that the detector can spatially distinguish between radiation coming from the different segments. Thus, an undesired interference of detection signals originating from portions of the object of interest which have been hit by ultrasonic waves of the same frequency is securely avoided.

The electromagnetic radiation detector may be a frequency resolving detector, that is a detector capable of distinguishing between signals having different frequencies. Further, it is advantageous that the detector is capable of timely resolving signals.

The apparatus may further comprise a reconstruction unit adapted to reconstruct an image of the object of interest based on the detected electromagnetic fluorescence radiation. Since spatial information is encoded in the frequency information, geometrical or structural information can be reconstructed from the detection signals.

The reconstruction unit may particularly be adapted to reconstruct an image of the object of interest based on a frequency analysis, particularly on a Fourier analysis (like a Fourier transformation), of the detected electromagnetic fluorescence radiation. Such a Fourier analysis is capable of transforming the frequency spectrum into the inverse Fourier space.

The apparatus may comprise an electromagnetic radiation source adapted to emit electromagnetic radiation on the object of interest. As an alternative to the use of optical radiation, it is also possible to use electromagnetic radiation having other wavelengths, like infrared or ultraviolet radiation. The radiation used depends on the energy which is needed to force material of a portion of the object of interest to emit fluorescence radiation.

The electromagnetic radiation source may be adapted to emit electromagnetic radiation on the object of interest in a manner of one of the group consisting of a continuous manner, a modulated manner and a pulsed manner. The emission scheme of the electromagnetic radiation source should be synchronized with the emission scheme of the ultrasonic sound source. However, the provision of an electromagnetic radiation source is optional: alternatively or additionally, it is possible to use electromagnetic radiation from the environment, for instance daylight.

In the following, exemplary embodiments of the array for imaging an object of interest will be described. However, these embodiments also apply for the apparatus and for the method of imaging an object of interest, for the use according to the invention, for the computer-readable medium and for the program element.

The object of interest of the array may have attached a particle comprising a donor adapted to absorb electromagnetic radiation and/or an acceptor for emitting electromagnetic fluorescence radiation. The emission of electromagnetic fluorescence radiation by the particle may be based on a fluorescence resonant energy transfer process, for instance a FRET process.

According to the invention, ultrasonic-active microbubbles having an optically active donor and an acceptor may be attached to the object of interest. The donor may absorb electromagnetic radiation and may transfer the absorbed energy to the acceptor in such a manner that fluorescence radiation is emitted having another frequency than exciting electromagnetic radiation. The efficiency of the energy transfer process and thus of the emission of electromagnetic fluorescence radiation depends on the distance between acceptor and donor. According to the invention, ultrasonic radiation is used as a mechanical pressure wave which modulates the distance between acceptor and donor. Thus, the emitted fluorescence radiation has a contribution of the frequency of the ultrasonic source.

According to an embodiment of the invention, a two-dimensional matrix of transducers may be provided, wherein the amplitude and the phase of each transducer is individually adjustable.

In order to avoid an undesired overlap of different foci, it is possible to arrange the different foci not directly adjacent to one another, but to arrange them on nodes of a two-dimensional lattice or a three-dimensional lattice, wherein the distance between adjacent nodes may be larger than the dimension of a focus.

The aspects defined above and further aspects of the invention are apparent from the examples of embodiment to be described hereinafter and are explained with reference to these examples of embodiment.

The invention will be described in more detail hereinafter with reference to examples of embodiment but to which the invention is not limited.

The illustration in the drawing is schematically. In different drawings, similar or identical elements are provided with the same reference signs.

In the following, referring to FIG. 1A, a principle of fluorescence on a compressed vascular particle according to an embodiment of the invention will be described.

Figure 1A:
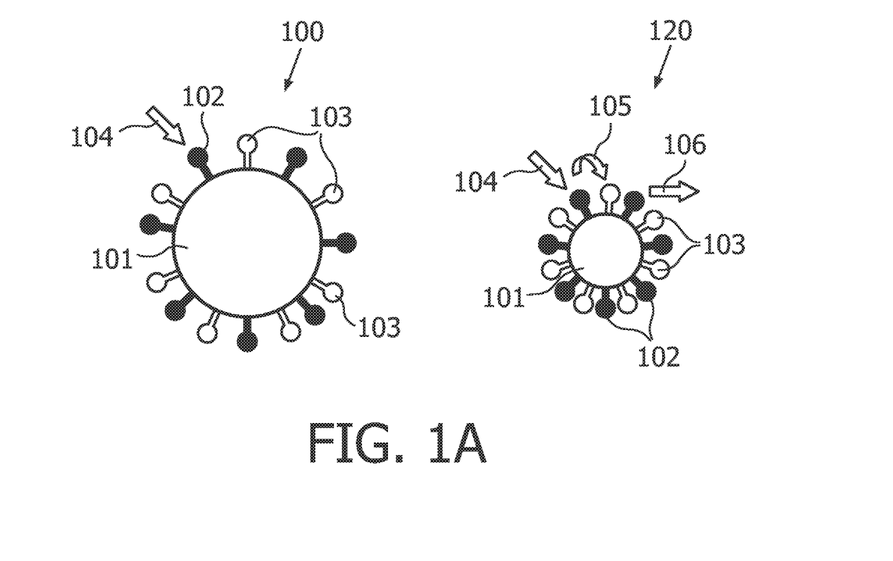
FIG. 1A shows a principle of fluorescence on a compressed spherical vesicular particle in accordance with an exemplary embodiment of the invention.

FIG. 1A shows a particle 101 in a first state 100 and in a second state 120. In the first state 100, the particle 101 (e.g. a vesicle) is shown in a relaxed state: A donor molecule 102 absorbs energy from excitation light 104, but since the vesicle 101 is in a relaxed state, the distance between the donor 102 and an acceptor 103 (which is capable of emitting optical fluorescence radiation when provided with energy from the donor 102) is too large for an efficient energy transfer.

In contrast to this, in the second state 120, a compressed or deformed state of the particle 101 is shown. Herein, the energy from the excitation light 104 is transferred from the donor 102 to the acceptor 103 (see bent arrow 105), and the acceptor 103 emits fluorescence light 106.

A compression of the particle 101 may be achieved, according to the invention, by emitting ultrasonic waves onto the particle 101 causing the particle 101 to mechanically oscillate, such that a transition between the relaxed state 100 and the compressed state 120 occurs.

Figure 1B:
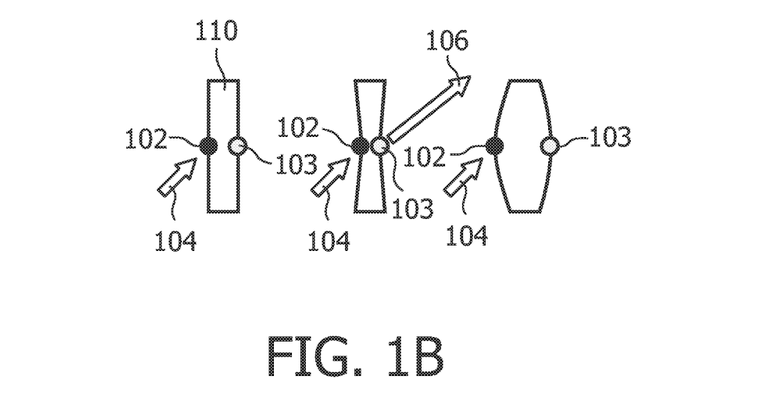
FIG. 1B illustrates an alternative embodiment in which a particle has a rectangular or rod-like shape.

FIG. 1B shows an alternative embodiment of a particle 110, namely showing a rectangular particle 110 in a relaxed state and in two different excitation states.

Figure 2:
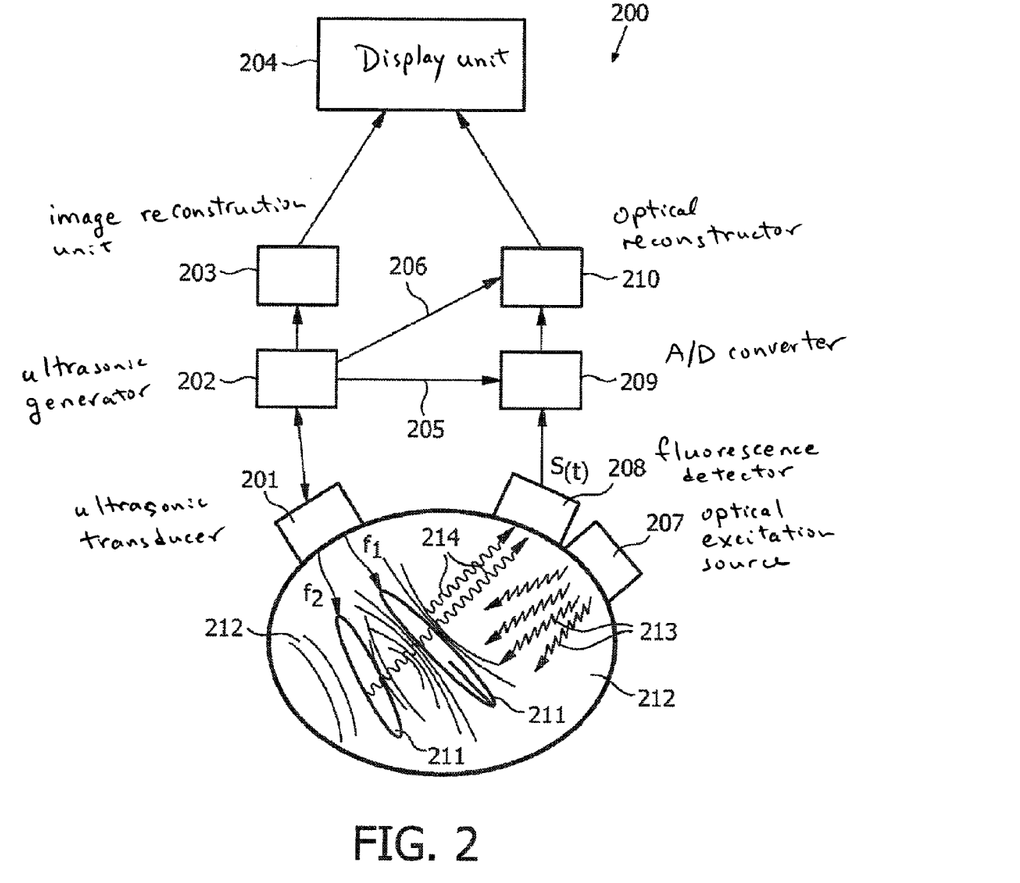
FIG. 2 illustrates an array for imaging an object of interest according to an exemplary embodiment of the invention.

In the following, referring to FIG. 2, an imaging array 200 according to an exemplary embodiment of the invention will be described.

Particles 211 including fluorescent donors and acceptors (not shown) have been introduced into an object of interest 212 such as a body organ, a body of a human or animal patient or any other object which is to be imaged. The apparatus 200 provides an ultrasound image of the body 212 as well as a fluorescence image with a contrast determined by the concentration of the particles 211. For the ultrasound image, a linear ultrasound transducer array 201 transmits an ultrasound pulse of few wave lengths as is used for ordinary B-mode imaging.

The ultrasonic transducer 201 is adapted to emit ultrasonic waves of different frequencies f1 and f2 to different positions within the object of interest 212. Since the two particles 211 shown in FIG. 2 are arranged at different locations within the object of interest 212, ultrasonic waves impinging on the two particles 211 have different frequencies f1 and f2. As the pulse travels to the object of interest 212, reflections on internal surfaces produce an echo signal received by the transducer 201. The ultrasound receive unit 202 transfers the echo into a one-dimensional ultrasound image. The ultrasound image reconstruction unit 203 collects one-dimensional ultrasound images and calculates a two-dimensional image from it that may be displayed by a display unit 204.

The fluorescence image is formed parallel to this as described in the following. As the ultrasound pulse traverses the object of interest 212, it causes oscillations of the particles 211 along its path. Particles 211 which are hit by ultrasonic waves with the different frequencies f1 and f2 oscillate accordingly with different frequencies.

One or more optical excitation sources 207 provides or provide excitation light 213 with a spectral overlap with the absorption spectrum of the donor of the particles 211 of the object of interest 212.

The light source 207 can be continuous or pulsed, e.g. continuous wave, modulated or pulsed with defined (variable) wavelengths. Acceptors on particles 211 subject to the oscillations produce a fluorescence signal 214 that is proportional to the local concentration of the particles 211 along the path of the pulse and which is modulated by the respective frequency f1 or f2. The fluorescence light 214 is detected by a photodiode or an array of photodiodes 208 which are directly attached to the object of interest 212 in order to collect as much of the fluorescence light 214 as possible. The diode array 208 may cover as much as possible of the body surface for the same purpose. The light input of the photodiodes 208 may be equipped with an optical filter that blocks light having the wavelength defined by the optical excitation source 207 and preferably passes only the fluorescence light so that background radiation is suppressed to avoid a disturbance of the signal.

The signals detected by the photodiodes 208 may be summed and the summed signal S(t) may be digitized by an analog/digital converter 209. Since a meaningful signal can be recorded only during the first transversal of the ultrasound pulse across the body after its transmission, the operation of the A/D converter 209 may be gated by the ultrasound generation unit 202 by means of a gate signal 205. Preferably, the gate signal 205 starts sampling at a time of transmission of the ultrasound pulse and stops sampling after the pulse has either traversed the entire body 212 or after the pulse has been attenuated so much that no useful signal can be recorded any more, whatever time is shorter. These times can be calculated from the size of the body 212 and the attenuation depths of the ultrasound beams. The optical reconstruction unit 210 transfers the signal S(t) into a one-dimensional fluorescence image.

In order to improve the resolution among the beam path, the signal can be de-convoluted with a pulse shape of the ultrasound pulse provided by the ultrasound generation unit 202 on a data connection 206. The optical image reconstruction unit 210 collects the one-dimensional optical images and calculates a two-dimensional image from it, that may be displayed by the display unit 204.

The optical image reconstruction unit 210 performs a frequency analysis, particularly a Fourier transformation, to distinguish between the signals originating from different particles 211 and being modulated with different ultrasonic wave frequencies f1 or f2. Thus, a spatial resolution can be reconstructed due to the knowledge of the frequencies f1, f2 of the exciting ultrasonic waves.

The display unit 204 may either display the ultrasound image and the optical image separately or a combination of both, e.g. a color overlay of the optical image to the ultrasound image.

Thus, the imaging array 200 is adapted for imaging the object of interest 212 and has the ultrasound device 201 being adapted to emit ultrasonic waves of two different frequencies f1, f2 onto the object of interest 212. The optical detector 208 is adapted to detect fluorescence light emitted by the object of interest 212 in response to an absorption of light from the light source 207 and in response to the respective ultrasonic waves. The ultrasound device 201 is adapted as a multi-frequency ultrasound device and is capable of emitting ultrasonic waves of the different frequencies f1, f2 towards the two different portions 211 of the object of interest 212 in such a manner that the electromagnetic fluorescence radiation 214 emitted by the two different portions 211 of the object of interest 212 has to two different frequency contributions. The ultrasound device 201 emits ultrasonic waves onto the object of interest 212 in such a manner that an amplitude and a phase of the emission of ultrasonic waves is controllable separately for the two particles 211. The ultrasound device 201 emits ultrasonic waves of the two different frequencies f1, f2 in different spatial directions as to impinge on the different particles 211. The electromagnetic radiation detector 208 is a non-spatially resolving detector, that is the signal contributions originating from the different particles 211 are separated via the frequency.

The optical reconstruction unit 210 reconstructs an image of the object of interest 211 based on the detected electromagnetic fluorescence radiation. For this purpose, a Fourier analysis of the detected electromagnetic fluorescence radiation is performed by the optical reconstruction unit 210. The particles 211 having FRET donors and acceptors can be realized as shown in FIG. 1A or in FIG. 1B.

Figure 3:
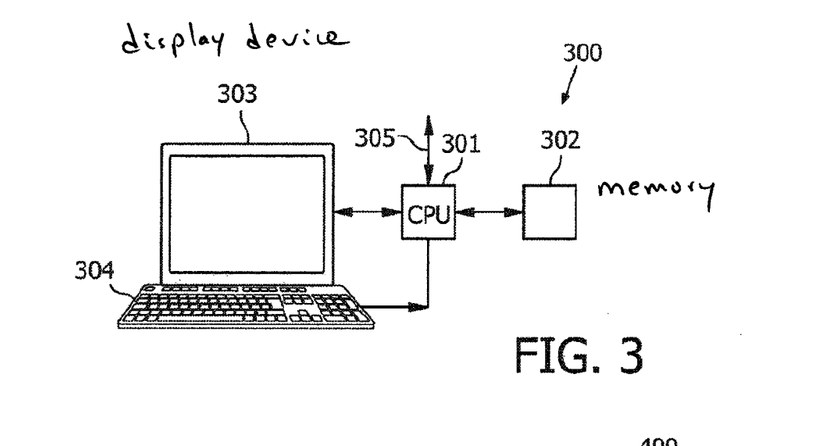
FIG. 3 is a schematic block diagram of a computer system for controlling an apparatus for combined ultrasound and fluorescence imaging according to an embodiment of the invention.

FIG. 3 depicts an exemplary embodiment of a data processing device 300 according to the present invention for executing an exemplary embodiment of a method in accordance with the present invention. The data processing device 300 depicted in FIG. 3 comprises a central processing unit (CPU) or image processor 301 connected to a memory 302 for storing an image depicting an object of interest, such as a patient. The data processor 301 may be connected to a plurality of input/output network or diagnosis services, such as an apparatus for imaging an object of interest. The data processor 301 may furthermore be connected to a display unit 303, for example a computer monitor, for displaying information on an image computed or adapted in the data processor 301. An operator or user may interact with the data processor 301 via a keyboard 304 and/or other output devices, which are not depicted in FIG. 3. Furthermore, via the bus system 305, it is also possible to connect the image processing control processor 301 to, for example, a motion monitor, which monitors a motion of the object of interest. In case, for example, a lung of a patient is imaged, the motion sensor may be an exhalation sensor. In case the heart is imaged, the motion sensor may be an electrocardiogram (ECG).

Exemplary technical fields, in which the invention may be applied advantageously, include medical applications, material testing, and material science. An improved image quality and a reduced amount of calculations in combination with a low effort may be achieved. Also, the invention can be applied in the field of heart scanning to detect heart diseases.

In the following, referring to FIG. 4, an imaging array 400 according to another exemplary embodiment of the invention will be described.

The imaging array 400 for imaging an object of interest comprises a first portion 401 located at a position x1 along an extension direction 403 and a second portion 402 located at a position x2 along the extension direction 403. The apparatus 400 comprises a multi-frequency ultrasound device 404 which is capable of emitting ultrasonic waves 405 of two different frequencies f1 and f2 onto the portions 401, 402 of the object under examination. In more detail, ultrasonic waves 405 having a frequency f1 are directed to the first portion 401, and ultrasonic waves 405 having a second frequency f2 are directed onto the second portion 402. Further, the apparatus 400 comprises an electromagnetic radiation detector 406 which is capable of detecting electromagnetic fluorescence radiation 407 emitted by the first and the second portions 401, 402 of the object of interest in response to the absorption of primary electromagnetic radiation emitted by an electromagnetic radiation source 408 and in response to the ultrasonic waves 405. The electromagnetic radiation source 408 is provided which emits electromagnetic radiation 409 onto the first portion 401 and onto the second portion 402.

Figure 4:
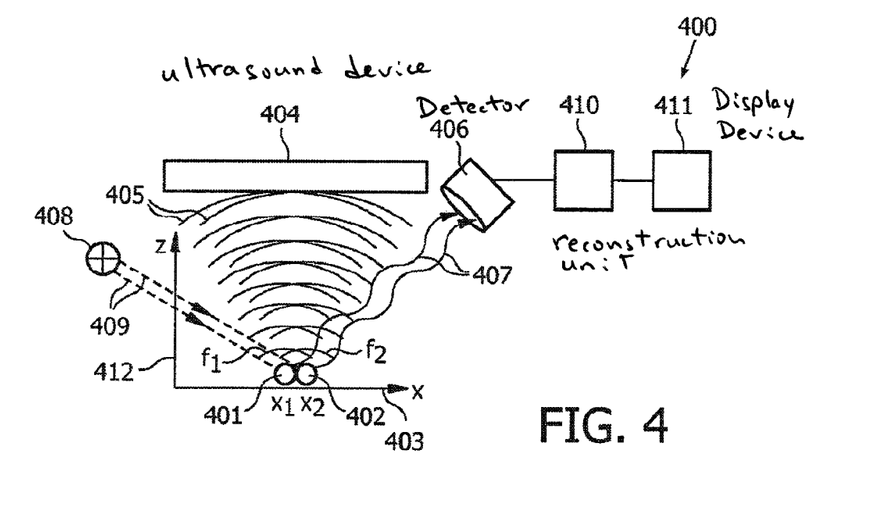
FIG. 4 is a schematic illustration of an array for imaging an object of interest according to another exemplary embodiment of the invention.

Although not shown in FIG. 4, the first and second portions 401, 402 of the object of interest are provided with acceptors and donors in a manner shown in FIG. 1A, so that the ultrasonic waves 405 cause a deformation/oscillation of particles having such acceptors and donors, which results in a modulation of the re-emitted fluorescence radiation.

Electromagnetic radiation from the electromagnetic radiation source 408 is generated with such a wavelength that it is possible in a particular compression state of the particles attached to the first and second portions 401, 402 to absorb the electromagnetic radiation 409. When the compression state caused by the ultrasonic waves 405 in the first or the second portion 401, 402 is such that the distance between donors and acceptors is sufficiently small (i.e. in a particular mechanical vibration phase state), then an energy transfer from the donor to the acceptor is possible which causes the acceptor to re-emit fluorescence radiation 407. This fluorescence radiation 407 carries a fingerprint of the respective frequency f1 or f2 of the ultrasonic waves 405 impinging on a particular one of the portions 401, 402. Thus, the detection signals detected by the electromagnetic radiation detector 406 has characteristic frequency contributions in correspondence with the ultrasonic frequencies f1, f2, so that a Fourier analysis of the detection spectrum allows to reconstruct the spatial distribution of the portions 401, 402 of the object of interest.

As shown in FIG. 4, the ultrasound device 404 is adapted to emit ultrasonic waves of the two different frequencies f1, f2 on the two different portions 401, 402 of the object of interest concurrently, that is to say simultaneously. Since the mechanical frequency with which the particles of the portions 401, 402 oscillate depends on the exciting ultrasonic waves, the fluorescence radiation has different frequency contributions.

The ultrasound device 404 is realized as a single ultrasound source which is adapted to emit ultrasonic waves of the two different frequencies f1, f2 in different spatial directions such as to impinge a particular one of the portions 401, 402 at positions x1 and x2.

A reconstruction unit 410 which is coupled to an output of the electromagnetic radiation detector 406 reconstructs the image of the object of interest, that is to say a position of the portions 401, 402 based on a Fourier transformation of the detected electromagnetic fluorescence radiation. These data are provided to a display device 411 for displaying the reconstructed image.

Thus, FIG. 4 illustrates a principle of using frequency encoding to parallelize optical imaging rather than imaging point by point. The ultrasonic transducer 404 simultaneously emits two ultrasonic fields at distant frequencies f1 and f2, which are designed to form two foci adjacent along the axis 403. Each of these foci then emits an optical fluorescence signal 407 which is modulated by the respective ultrasonic frequency f1 or f2. After optical detection by the electromagnetic radiation detector 406, a Fourier transformation performed in the reconstruction unit 410 resolves these frequency components which can be attributed to their source locations x1 and x2, as shown in FIG. 5.

Figure 5:
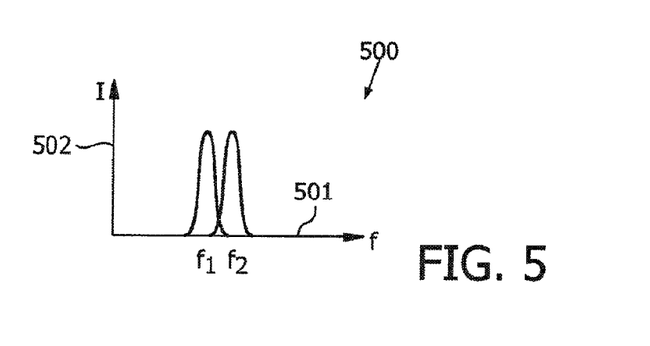
FIG. 5 is a diagram illustrating a reconstruction of an image of an object of interest using the array shown in FIG. 4.

FIG. 5 shows a diagram 500 having an abscissa 501 along which the modulation frequency f is shown. Along an ordinate 502, the intensity of the optical signal (which is proportional to the amount of material provided with particles and located at a particular position x along the axis 403 is shown.

Thus, the shape of the detection signals shown in FIG. 5 is a mapping of the material distribution along the x-axis 403. The intensity along the ordinate 502 is a mapping of the z-direction 412 shown in FIG. 4.

Figure 6:
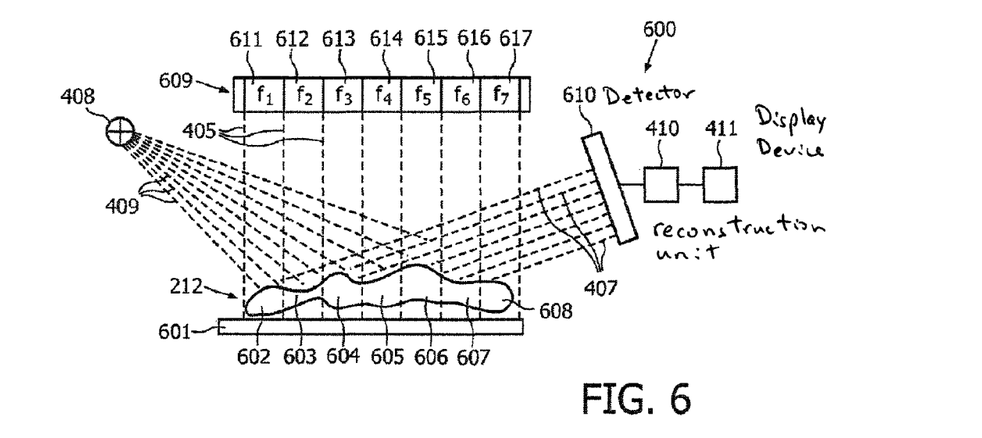
FIG. 6 illustrates an array for imaging an object of interest according to an alternative embodiment of the invention.

In the following, referring to FIG. 6, an imaging array 600 according to another exemplary embodiment of the invention will be described.

An object of interest 212 to be imaged is arranged on a mounting table 601. The object of interest 212 is divided (virtually) into first to seventh portions 602 to 608. An ultrasound transducer 609 is provided for generating ultrasound waves 405 which impinge on the different portions 602 to 608 of the object of interest 212. Each portion 602 to 608 is irradiated by a particular frequency f1 to f7 of ultrasonic waves, each generated by a particular one of first to seventh transducer sources 611 to 617.

An electromagnetic radiation source 408 generates essentially monochromatic excitation radiation 409 which impinges on all of the portions 602 to 608. All portions 602 to 608 of the object of interest 212 are provided with donors and acceptors located in a particular distance from one another. This distance is modulated by the mechanical oscillations generated by the first to seventh transducer sources 611 to 617, so that in a particular compression state of the mechanically oscillating particles, a distance between donor and acceptor is sufficiently small to allow an energy transfer from absorbed electromagnetic radiation 409 absorbed by a donor to an acceptor to generate fluorescence light 407. In another particular compression state of the mechanically oscillating particles, a distance between donor and acceptor is too large to allow an energy transfer from absorbed electromagnetic radiation 409 absorbed by a donor to an acceptor so that no fluorescence light 407 is generated in this state.

Generated fluorescence light 407 is detected by a non-spatially resolving electromagnetic radiation detector 610. However, the fluorescence signals of the different portions 601 to 608 are separable by the different modulation frequencies f1 to f7. In a reconstruction unit 410, a Fourier analysis is performed to separate the different frequency contributions and to reconstruct an image which is displayed on a display device 411.

In the following, referring to FIG. 7, an imaging array 700 according to an alternative embodiment of the invention will be described.

Figure 7:
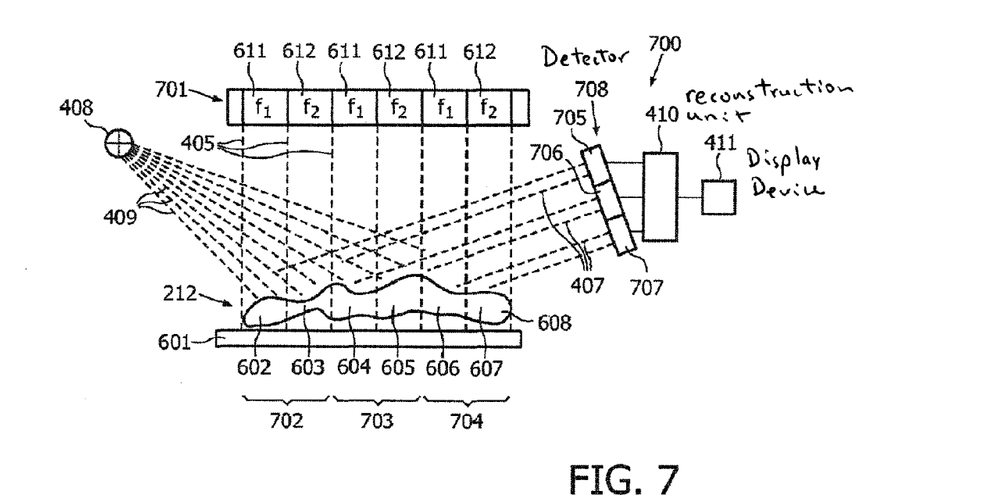
FIG. 7 illustrates an array for imaging an object of interest according to a further alternative embodiment of the invention.

The imaging array 700 differs from the imaging array 600 in that an ultrasound transducer 701 is provided having six different ultrasonic sources which are arranged linearly and which are adapted to emit ultrasonic waves having the frequency f1 or f2 (see FIG. 7). The object of interest 212 is divided (virtually) into six portions 602 to 607, wherein a first portion 602 and a second portion 603 form a first segment 702, a third portion 604 and a forth portion 605 form a second segment 703, and a fifth portion 606 and a six portion 607 form a third segment 704. Different portions within a single one of the segments are irradiated with ultrasonic waves having different frequencies. However, different portions of different segments may be irradiated with identical ultrasonic frequencies.

According to the embodiment shown in FIG. 7, the detector 708 is realized as a spatially resolving electromagnetic radiation detector 708 capable of spatially distinguishing between fluorescence radiation 704 originating from the three segments 702 to 704. In more detail, fluorescence radiation 704 originating from the first segment 702 is detected geometrically by a first detector portion 705, radiation coming from the second segment 703 is detected geometrically by a second detector portion 706, and radiation originating from the third segment 704 is detected by a third detector portion 707. The output of the detector 708 is provided to a reconstruction unit 410, wherein the results, that is the image to be reproduced, is displayed on the display 411.

Within a particular segment 702 to 704, different portions 602 to 607 of the object of interest 212 are irradiated with ultrasonic waves having different frequencies. However, according to the spatial resolution of the detector 708, it is possible to use only two ultrasonic frequencies f1, f2.

In the following, exemplary embodiments of particles having donors and acceptors will be described.

A donor or an acceptor can be any of a molecule, a group of molecules, a complex of the types and examples of donors and acceptors being referred to in the present invention.

The particles may be deformable or flexible. The particles may be globular particles such as vesicles. "Vesicle" refers to an entity which generally has one or more walls or membranes which form one or more internal voids. Vesicles may be formulated, for example, from a stabilizing material such as a lipid, a protein, a polymer, a surfactant and/or a carbohydrate. The lipids, proteins, polymers, surfactants and/or other vesicle forming stabilizing material may be natural, synthetic or semi-synthetic. The walls or membranes may be concentric or otherwise. The stabilizing compounds may be in the form of one or more monolayer or bilayer. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The internal void of the vesicles may be filled with a wide variety of liquid, gases or solid materials (or combinations thereof) including, for example, water, oils, fluorinated oils, gases, gases precursors, liquids, and fluorinated liquids, if desired, and/or other materials. The vesicles may also comprise a photoactive agent, a bioactive or pharmaceutical compound and/or a targeting ligand, if desired.

Globular particles which are particles suitable for the compounds and methods of the invention are preferably biocompatible and/or highly compressable or expendable. Examples are micro-bubbles. These can be small, 3 to 5 µm diameter, gas filled spheres that provide their enhancement through several mechanisms linked to their high compressibility when exposed to an ultrasonic pressure field (see De Jong, N et al. in Ultrasonics, 1996, 34 (2 to 5): pp. 587 to 590; Moran, C M et al. in Ultrasound in Medicine & Biology, 2002, 28 (6): pp. 785 to 791. Available ultrasound contrast agents are for instance Definity™, marketed by Bristol-Myers-Squibb and developed by Unger at ImaRX, consist of 1.1 to 3.3 micron diameter spheres with a lipid shell and octafluoropropane gas interior. Optison™, marketed by Amersham and originally developed by Mallinckrodt, contains spheres with diameters ranging from 2 to 4.5 microns, albumin shells, and containing octafluoropropane gas. Albunex™, also marketed by Amersham, is a first generation agent similar to Optison™, but containing room air. Sonovue™, marketed by Bracco, is a phospholipid coated sulphur hexafluoride micro-bubble with a mean size of 2.5 microns. Echovist™ and Levovist™, marketed by Schering, have been in use for some time and consist of sugar stabilized room air micro-bubbles with less controlled size distributions (larger than 5 µm).

The physical mechanism for ultrasound contrast involves the high compressibility of the gas within the bubble and the physical size of the bubble (de Jong cited supra; Harvey, C J et al. in Advances in Ultrasound, Clinical Radiology, 2002, 57 (3), pp. 157 to 177, Callida, F et al. in Ultrasound contrast agents: Basic principles, European Journal of Radiology, 1998, 27 (2): pp. 157 to 160. At diagnostic imaging frequencies, the micro-bubbles can undergo oscillations that are many multiples of the resting diameters. This effect is especially exaggerated near the resonance of the gas bubble. By careful choice of the gas within the micro-bubble and the elastic characteristics of the shell material, the stability of the bubble and this contrast effect can be manipulated.

Also liposomes are potentially useful contrast agents for ultrasound imaging. Liposomes have been used for more than 25 years as a potential mechanism for drug delivery. Most liposomes are not echogenic, consisting primarily of fat. Usually liposomes consist of non-gaseous, multi-lamellar acoustically reflective lipids (Demos, S et al., Journal of the American College of Cardiology, 1999, 33: pp. 867 to 875). These liposomes are characterized by the presence of many small and irregularly shaped vesicles arranged in a "raspberry-like" appearance. The liposomes are typically smaller than 1 micron in diameter. The usage of liposomes results in an enhanced appearance in ultrasound imaging due to scattering process. Liposomes however have a low stability and half-life and no major mechanical resonance is connected with liposomes.

According to another embodiment of the invention, the particles are micellar. Micelle refers to a colloidal entity formulated from lipids. In exemplary embodiments, miscelles comprise a monolayer, bilayer or hexagonal H II phase structure, see U.S. Pat. No. 6,033,645.

Particles with other shapes than globular shapes can be deformed via ultrasound in order to change the distance between fluorescence donor and acceptor molecules which are present on the particle. Non-globular particles which are suitable for the compounds and the methods of the invention are rod-like or Y-shaped, tubular or rectangular.

According to another embodiment of the invention, the particles are aerogels. Aerogels refers to generally spherical or spheroidal entities which are characterized by plurality of small internal voids, see U.S. Pat. No. 6,106,474. The aerogels may be formulated from synthetic materials (for example, a foam prepared from baking resorcinol and formaldehyde), as well as natural materials, such a carbohydrates (polysaccharides) or proteins.

According to another embodiment of the invention, the particles are clathrates. Clathrate refers to a solid, semi-porous or porous particle which may be associated with vesicles. In an exemplary form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acids precipitated with calcium salts, see U.S. Pat. No. 5,086,620.

In accordance with a method of the invention, the particles are subjected to an ultrasound field, resulting in a deformation and/or oscillation of the particles. Ultrasonic waves are longitudinal compression waves. For longitudinal waves, the displacement of the particles in the medium is parallel to the direction of wave motion as opposed to transfer waves for which the displacement is perpendicular to the direction of propagation. Ultrasound particularly refers to any frequency at the high end or above the audible spectrum of the human ear (20 Hz to 20 kHz). Medical imaging uses typical frequencies of about 2.5 MHz. According to the present invention, lower or higher frequencies can be selected as desired, depending on the type of tissue being examined in the type of particles being used. A commonly used parameter in ultrasound imaging is the mechanical index (=peak refractional or negative pressure divided by the square root of the ultrasound frequency). The mechanical index is related to the peak negative pressure in the tissue and thus relates to the stiffness of the particles which can be used and still provide enough deformation to achieve an effect used in embodiments of the invention. Clinical values of the MI are between 1 and 2. In a particular embodiment, globular particles of the present invention can be compressed in volume by a factor of between at least 5, to about 10, 25, 50 or 100, in order to bring fluorescence donor and acceptor molecules into each other's proximity. In another particular embodiment, globular particles of the present invention can be expended in volume by a factor of between at least 5, to about 10, 25, 50, or 100, in order to move donor and acceptor molecules away from each other.

According to an embodiment of the invention, the fluorescence donors and acceptors on the particles of the present invention may exchange energy via FRET (fluorescence resonance energy transfer). FRET is the transfer of the excited state energy from a donor to an acceptor, and can occur when the emission spectrum of a donor fluorophore overlaps the absorption spectrum of the acceptor fluorophore. Thus, by exciting at the absorption maximum of the donor and monitoring the emission at the long wavelength side of the acceptor fluorophore, it is possible to monitor only donor and acceptor molecules that are bound and reside within a certain distance.

Examples of useful donor-acceptor pairs include NBD (that is N-(7-nitrobenz-2-oxa-1,3-diacol-4-yl)) to rhodamine, NBD to fluoroscein to eosin or erythrosine, dansyl to rhodamine, and acridine orange to rhodamine. Examples of suitable commercially available labels capable of exhibiting FRET include fluoroscein to tetramethylrhodamine, 4,4-difluoro-5,7-dimethyl-4-bora-3a,4a-diaza-s-indacene-3-propionic acid, succinimidyl ester, which is commercially available, for instance under the trade destination BODIPY FL from Molecular Probes (Eugene, Oreg.) to 4,4-difluoro-5-phenyl-4-bora-3a,4a-diaza-sindacene-3-propionicacid, succinimidyl ester, which is commercially available, for instance under the trade destination BODIPY R6G from Molecular Probes, Cy3.5 monofunctional NHS-ester to Cy5.5 monofunctional NHS-ester, Cy3 monofunctional NHS-ester to Cy5 monofunctional NHS-ester, and Cy5 monofunctional NHS-ester to Cy7 monofunctional NHS-ester, all of which are commercially available from Amersham Biosciences (Buckinghamshire, England), and ALEXA FLUOR 555 carboxylic acid, succinimidyl ester to ALEXA FLUOR 647 carboxylic acid, succinimidyl ester, which are commercially available from Molecular Probes.

Other examples of molecules that are used in FRET include the fluorescein derivates such as 5-carboxyfluorescein (5-FAM), 6-carboxyfluorescein (6-FAM), fluorescein-5-isothiocyanate (FITC), 2'7'-dimethoxy-4'5'-difluoro-6-carboxyfluorescein (JOE), rhodamine derivates such as N,N,N', N'-tetramethyl-6-carboxyrhodamine (TAMRA), 6-carboxyrhodamine (R6G), tetramethyl-indocarbocyanine (Cy3), tetramethyl-benzindocarbocyanine (Cy3.5), tetramethyl-indodicarbocyanine (Cy5), tetramethyl-indotricarbocyanine (Cy7), 6-carboxy-X-rhodamine (ROX), hexachlorofluorescein (HEX), tetrachlorofluorescein TET, R-phycoerythrin, 4-(4'-dimethylaminophenylaz-o) benzoic acids (DABCYL), and 5-(2'-aminoethyl)aminonaphthalene-1-sulfonic acid (EDANS).

Further FRET donor and acceptor molecules which are particular suitable for the methods of the present invention are fluorescent proteins, e.g. dsRed, GFP (Green Fluorescent Protein) or its variants EYFP (Enhanced Yellow Fluorescent Protein), ECFP (Enhanced Cyan Fluorescent Protein), EBFP (Enhanced Blue Fluorescent Protein).

The fluorescence donor and acceptor pairs for FRET can be localized on the outside of a particle, on the inside of a particle or can be embedded in the particle membrane or particle shell. In particular embodiments, the donor is on the inside of the particle while the acceptor is on the outside or in the wall of the particle or the like. The fluorescence donor and acceptor pairs for energy exchange via FRET can be covalently bound to the particle or can be reversible bound to the particle via ionic interactions or via hydrophilic binding. In particular embodiments, the donor and the acceptor are on the inside or on the outside of the particle. The compression and extension of such a bubble brings donor and acceptor respectively into each other's proximity, or separates them from each other.

In a particular embodiment, the fluorescence donor and acceptor molecules are covalently bound to the ultrasonic particles or to the compounds used for the manufacture of the compounds. In another embodiment, the fluorescence donor and acceptor do not reside on the ultrasonic particle. For example, donor and/or acceptor molecules may be injected whereafter the bubbles take up the dye in the tissue. It is also possible, to inject quenchers or the like. All these chemicals may react with the tissue either to become active or inactive.

In another embodiment, the fluorescence acceptor and/or donor binds weakly to the ultrasound particle.

In a particular embodiment, the particles further comprise additional compounds or agents such as compounds or agents for targeting the complete particle to a tissue or a cell type for example via tissue or cell-specific bioagents, for example monoclonal or polyclonal antibodies. An example hereof is a particle having antibodies to a bacterium or a virus, allowing a sensitive and specific detection of infections using ultrasound.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

LIST OF REFERENCE 100 first state
101 spherical particle
102 donor
103 acceptor
104 excitation light
105 bent arrow
106 acceptor fluorescence
120 second state
130 rectangular particle
200 imaging array
201 ultrasonic transducer
202 ultrasonic generator
203 image reconstruction unit
204 display unit
205 gating signal
206 ultrasonic envelope signal
207 optical excitation source
208 fluorescence detector
209 analog/digital converter
210 optical reconstructor
211 particles with FRET donors and acceptors
212 object of interest
213 optical excitation light
214 fluorescence light
300 data processing device
301 central processing unit
302 memory
303 display device
304 keyboard
305 bus system
400 imaging array
401 first portion
402 second portion
403 extension direction
404 multi-frequency ultrasound device
405 ultrasonic waves
406 electromagnetic radiation detector
407 electromagnetic fluorescence radiation
408 electromagnetic radiation source
409 electromagnetic radiation
410 reconstruction unit
411 display device
412 z-direction
500 diagram
501 abscissa
502 ordinate
600 imaging array
601 mounting table
602 first portion
603 second portion
604 third portion
605 forth portion
606 fifth portion
607 sixth portion
608 seventh portion
609 ultrasound transducer
610 non-spatially resolving electromagnetic radiation detector
611 first transducer source
612 second transducer source
613 third transducer source
614 forth transducer source
615 fifth transducer source
616 sixth transducer source
617 seventh transducer source
700 imaging array
701 ultrasound transducer
702 first segment
703 second segment
704 third segment
705 first detector portion
706 second detector portion
707 third detector portion
708 spatially resolving electromagnetic radiation detector

The invention claimed is:

1. An apparatus for imaging an object of interest including a particle, the apparatus comprising:
an ultrasound device configured to emit an ultrasound pulse including ultrasonic waves of at least two frequencies onto the object of interest;
a primary radiation source for emitting a primary electromagnetic radiation for absorption by a donor molecule of the particle;
an electromagnetic radiation detector configured to detect a signal including electromagnetic fluorescence radiation emitted by the object of interest in response to an absorption of the primary electromagnetic radiation and in response to the ultrasonic waves that are configured to decrease a distance between the donor molecule and an acceptor molecule of the particle for allowing energy transfer from the donor molecule to the acceptor molecule and emission of the electromagnetic fluorescence radiation by the acceptor molecule in response to the energy transfer; and a computer processor configured to form a de-convolved signal by de-convolving the signal detected by the electromagnetic radiation detector with the ultrasound pulse, the de-convolved signal being used for reconstructing an image for display.

2. The apparatus according to claim 1, wherein the ultrasound device is configured to emit the ultrasonic waves of the at least two frequencies on at least two different portions of the object of interest in such a manner that adjacent ones of the portions are spaced from one another by a predetermined distance and that a region between adjacent portions is free from an irradiation with ultrasonic waves.

3. The apparatus according to claim 2, wherein the ultrasound device is configured to emit the ultrasonic waves in such a manner that the at least two different portions being irradiated by ultrasonic waves are arranged to form a two-dimensional lattice or a three-dimensional lattice.

4. The apparatus according to claim 1, wherein the ultrasound device is divided into at least two separate ultrasound sources, wherein each of the at least two separate ultrasound sources is configured to emit ultrasonic waves of a particular frequency onto the object of interest.

5. The apparatus according to claim 4, wherein the at least two separate ultrasound sources are arranged linearly.

6. The apparatus according to claim 4, wherein the at least two separate ultrasound sources are arranged in a matrix-like manner.

7. The apparatus according to claim 4, wherein the at least two separate ultrasound sources are configured to emit ultrasonic waves of a particular frequency onto the object of interest in such a manner that an amplitude and a phase of the emission of ultrasonic waves is adjustable separately for each of the at least two separate ultrasound sources.

8. The apparatus according to claim 4, wherein the electromagnetic radiation detector is a spatially resolving detector, wherein at least two of the separate ultrasound sources are configured to emit ultrasonic waves of the same frequency onto at least two portions of the object of interest, the at least two portions are separated from one another by such a distance that electromagnetic fluorescence radiation originating from the at least two portions on which ultrasonic waves of the same frequency impinges is spatially distinguished by the electromagnetic radiation detector.

9. The apparatus according to claim 1, wherein the ultrasound device is realized as a single ultrasound source configured to emit the ultrasonic waves of the at least two different frequencies in different spatial directions towards at least two different portions of the object of interest.

10. The apparatus according to claim 1, wherein the manner in which the ultrasound device is further configured to emit the ultrasonic waves on the object of interest is selected from the group consisting of a continuous manner, a modulated manner and a pulsed manner.

11. The apparatus according to claim 1, wherein the electromagnetic radiation detector is a non-spatially resolving detector.

12. The apparatus according to claim 1, wherein the electromagnetic radiation detector is a frequency resolving detector.

13. The apparatus according to claim 1, comprising a reconstruction unit configured to reconstruct an image of the object of interest based on the detected electromagnetic fluorescence radiation.

14. The apparatus according to claim 13, wherein the reconstruction unit is configured to reconstruct the image of the object of interest based on a frequency analysis of the detected electromagnetic fluorescence radiation.

15. The apparatus according to claim 13, wherein the reconstruction unit is configured to reconstruct an image of the object of interest based on a Fourier analysis of the detected electromagnetic fluorescence radiation.

16. The apparatus according to claim 1, wherein the primary radiation source is configured to emit essentially monochromatic electromagnetic radiation on the object of interest.

17. The apparatus according to claim 1, wherein the primary radiation source is configured to emit optical light on the object of interest.

18. The apparatus according to claim 1, wherein the manner in which the primary radiation source is configured to emit the primary radiation on the object of interest is selected from the group consisting of a continuous manner, a modulated manner and a pulsed manner.

19. The apparatus of claim 1, wherein the ultrasound device is further configured to individually adjust directions and frequencies of the ultrasonic waves.

20. The apparatus of claim 1, wherein the object of interest includes micro-bubbles attached to the object of interest, and wherein the micro-bubbles are fluorescent only during exposure to an ultrasonic focus of the ultrasonic waves to define resolution of the imaging by a size of the ultrasonic focus.

21. The apparatus of claim 1, wherein the ultrasound device is further configured to emit the ultrasonic waves as ultrasound pulses, and wherein the signal detected by the electromagnetic radiation detector is digitized by an analog to digital converter which is gated by a gate signal that to start sampling at a time of transmission of the ultrasound pulse and stops sampling after the ultrasound pulse has traversed entirety of the object of interest.

22. The apparatus of claim 1, wherein the ultrasound device is further configured to concurrently emit the ultrasonic waves of the at least two frequencies on at least two different portions of the object of interest, the object of interest including a first portion and a second portion, the at least two frequencies including a first frequency and a second frequency, and wherein the ultrasound device is further configured to emit an ultrasonic wave at the first frequency on the first portion of the object of interest and concurrently emit an ultrasonic wave at the second frequency on the second portion of the object of interest such that the electromagnetic fluorescence radiation emitted by the first portion of the object of interest is modulated with the first frequency and the electromagnetic fluorescence radiation emitted by the second portion of the object of interest is modulated with the second frequency.

23. A method for imaging an object of interest including a particle, the method comprising the acts of:

emitting by a primary electromagnetic radiation source primary electromagnetic radiation for absorption by a donor molecule of the particle;

emitting an ultrasound pulse including ultrasonic waves of at least two frequencies onto the object of interest; and detecting a signal including an electromagnetic fluorescence radiation emitted by the object of interest in response to the absorption by the donor molecule of the primary electromagnetic radiation and in response to the ultrasonic waves;

forming a de-convolved signal by de-convolving the signal detected by the electromagnetic radiation detector with the ultrasound pulse; and displaying an image using the de-convolved signal, wherein the ultrasonic waves are configured to decrease a distance between the donor molecule and an acceptor molecule of the particle for allowing energy transfer from the donor molecule to the acceptor molecule and emission of the electromagnetic fluorescence radiation by the acceptor molecule in response to the energy transfer.

24. The method of claim 23, wherein the emitting act concurrently emits the ultrasonic waves of the at least two different frequencies on at least two different portions of the object of interest including a first portion and a second portion, and wherein the emitting act concurrently emits an ultrasonic wave at a first frequency on the first portion of the object of interest and an ultrasonic wave at a second frequency on the second portion of the object of interest such that the electromagnetic fluorescence radiation emitted by the first portion of the object of interest is modulated with the first frequency and the electromagnetic fluorescence radiation emitted by the second portion of the object of interest is modulated with the second frequency.

25. A tangible computer-readable medium, in which a computer program including non-transitory computer instructions for imaging an object of interest is stored which, when being executed by a computer processor, configures the computer processor to carry out the acts of:

causing a primary electromagnetic source to emit a primary electromagnetic radiation for absorption by a donor molecule of the particle;

causing an ultrasound device to emit an ultrasound pulse including ultrasonic waves of at least two frequencies onto the object of interest, the object of interest including a particle;

causing an electromagnetic radiation detector to detect a signal including electromagnetic fluorescence radiation emitted by the object of interest in response to the absorption by the donor molecule of the primary electromagnetic radiation and in response to the ultrasonic waves;

forming a de-convolved signal by de-convolving the signal detected by the electromagnetic radiation detector with the ultrasound pulse; and causing a display to display an image using the de-convolved signal, wherein the ultrasonic waves are configured to decrease a distance between the donor molecule and an acceptor molecule of the particle for allowing energy transfer from the donor molecule to the acceptor molecule and emission of the electromagnetic fluorescence radiation by the acceptor molecule in response to the energy transfer.

26. The tangible computer-readable medium of claim 25, wherein the emitting act concurrently emits the ultrasonic waves of the at least two frequencies on at least two different portions of the object of interest including a first portion and a second portion, and wherein the emitting act concurrently emits an ultrasonic wave at a first frequency on the first portion of the object of interest and an ultrasonic wave at a second frequency on the second portion of the object of interest such that the electromagnetic fluorescence radiation emitted by the first portion of the object of interest is modulated with the first frequency and the electromagnetic fluorescence radiation emitted by the second portion of the object of interest is modulated with the second frequency.

27. A non-transitory program element embedded in a tangible computer readable medium for imaging an object of interest including a particle, which, when being executed by a computer processor, configures the computer processor to carry out the acts of:

causing a primary electromagnetic source to emit a primary electromagnetic radiation for absorption by a donor molecule of the particle;

causing an ultrasound device to emit an ultrasound pulse including ultrasonic waves of at least two different frequencies onto the object of interest causing an electromagnetic radiation detector to detect a signal including electromagnetic fluorescence radiation emitted by the object of interest in response to the absorption by the donor molecule of the primary electromagnetic radiation and in response to the ultrasonic waves; and forming a de-convolved signal by de-convolving the signal detected by the electromagnetic radiation detector with the ultrasound pulse; and causing a display to display an image using the de-convolved signal, wherein the ultrasonic waves are configured to decrease a distance between the donor molecule and an acceptor molecule of the particle for allowing energy transfer from the donor molecule to the acceptor molecule and emission of the electromagnetic fluorescence radiation by the acceptor molecule in response to the energy transfer.

28. The non-transitory program element of claim 27, wherein the emitting act concurrently emits the ultrasonic waves of the at least two frequencies on at least two different portions of the object of interest including a first portion and a second portion, and wherein the emitting act concurrently emits an ultrasonic wave at a first frequency on the first portion of the object of interest and an ultrasonic wave at a second frequency on the second portion of the object of interest such that the electromagnetic fluorescence radiation emitted by the first portion of the object of interest is modulated with the first frequency and the electromagnetic fluorescence radiation emitted by the second portion of the object of interest is modulated with the second frequency.

* * * * *